United States Patent [19]

Nichols

[11] Patent Number: 5,337,760
[45] Date of Patent: Aug. 16, 1994

[54] HEAD HOLDER FOR BRAIN TOMOGRAPHY

[76] Inventor: Thomas K. Nichols, 365 Amity Rd., Andover, N.J. 07821

[21] Appl. No.: 982,098

[22] Filed: Nov. 25, 1992

[51] Int. Cl.⁵ .................. A61G 15/00; A47C 20/02
[52] U.S. Cl. .................. 128/845; 128/DIG. 15; 5/637
[58] Field of Search ............... 128/845, 846, 869–876, 128/DIG. 15; 602/5, 17, 32, 18, 33, 34, 35, 36, 37, 38, 39; 5/625, 636, 637

[56] References Cited

U.S. PATENT DOCUMENTS

| | | | |
|---|---|---|---|
| 2,386,134 | 10/1945 | Mermis | 128/845 |
| 4,182,322 | 1/1980 | Miller | 128/869 |
| 4,267,830 | 5/1981 | Vick | 128/870 |
| 4,400,820 | 8/1983 | O'Dell | 128/869 |
| 4,653,750 | 3/1987 | McIntyre | 128/869 |
| 4,655,206 | 4/1987 | Moody | 128/870 |
| 4,854,305 | 8/1989 | Bremer | 128/870 |
| 4,928,711 | 5/1990 | Williams | 128/870 |
| 5,207,716 | 5/1993 | McReynolds | 128/870 |
| 5,211,185 | 5/1993 | Garth | 128/870 |

OTHER PUBLICATIONS

GE Medical Systems Brain Tomography Holder User Notes, pp. 1–6.

*Primary Examiner*—Michael A. Brown
*Attorney, Agent, or Firm*—Synnestvedt & Lechner

[57] ABSTRACT

A head support assembly for immobilizing the head of a supine patient during brain tomography includes a mounting panel including mounting straps for securing the assembly to the patient support table of an imaging apparatus. A head frame assembly extends from one end of the panel and includes a pair of head frame elements having upstanding leg portions and horizontal head clamping portions. An adjustment screw connects the free ends of the head frame elements to permit the clamping of a patient's head therebetween. A head sling is suspended between the head clamping portions, being adjustably attached thereto by means of hook and loop fasteners. Forehead and chin restraining straps are also adjustably secured by means of hook and loop fasteners to the head frame elements. An optional neck support strap may also be attached to the head frame elements by means of hook and loop fasteners. The entire assembly is made of a non-metallic, imagable material, preferably a high strength composite, and provides a rigid immobilization of the head in a compact construction which permits close proximity of the camera to the patient's head for nuclear medicine imaging.

14 Claims, 3 Drawing Sheets

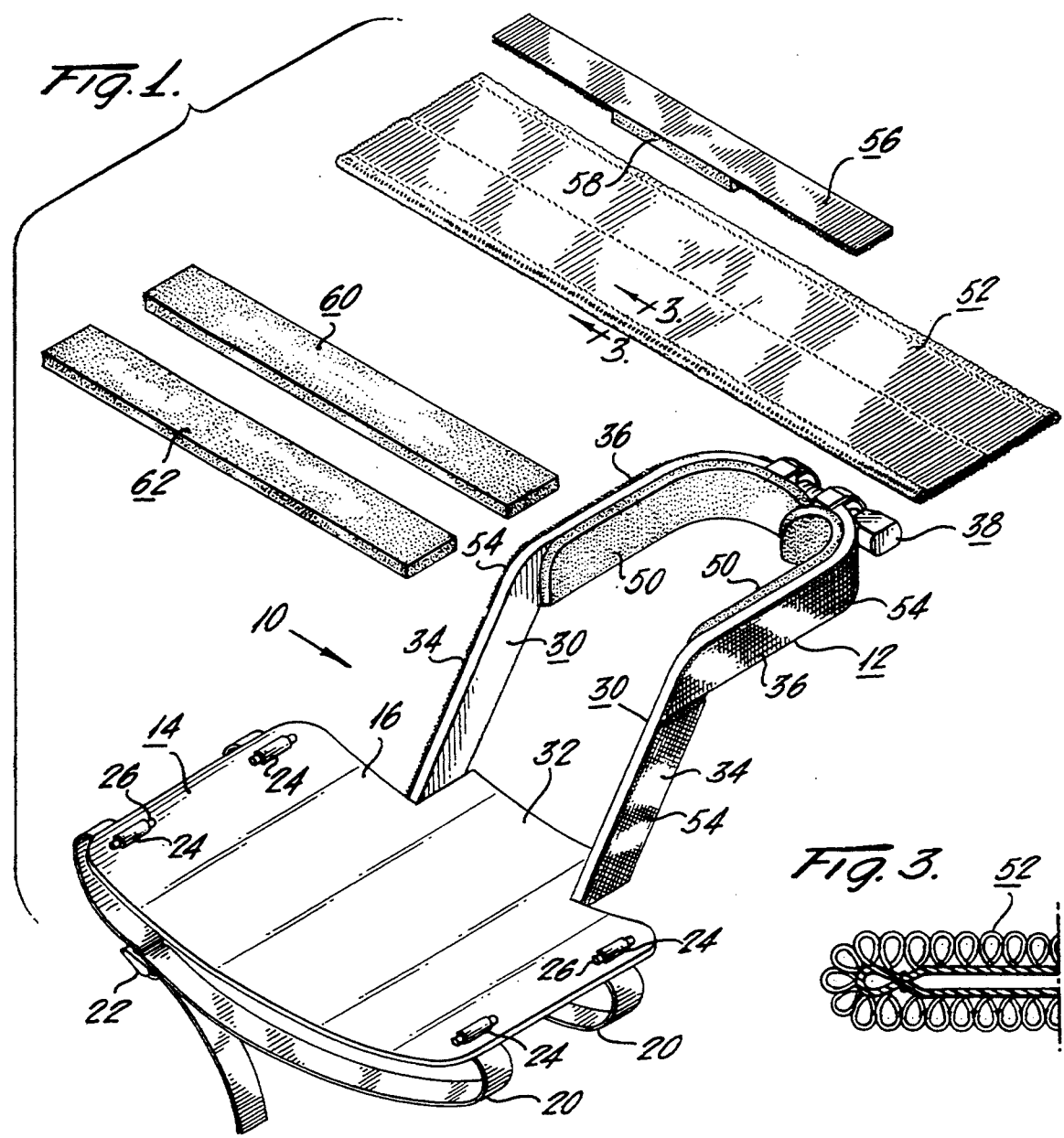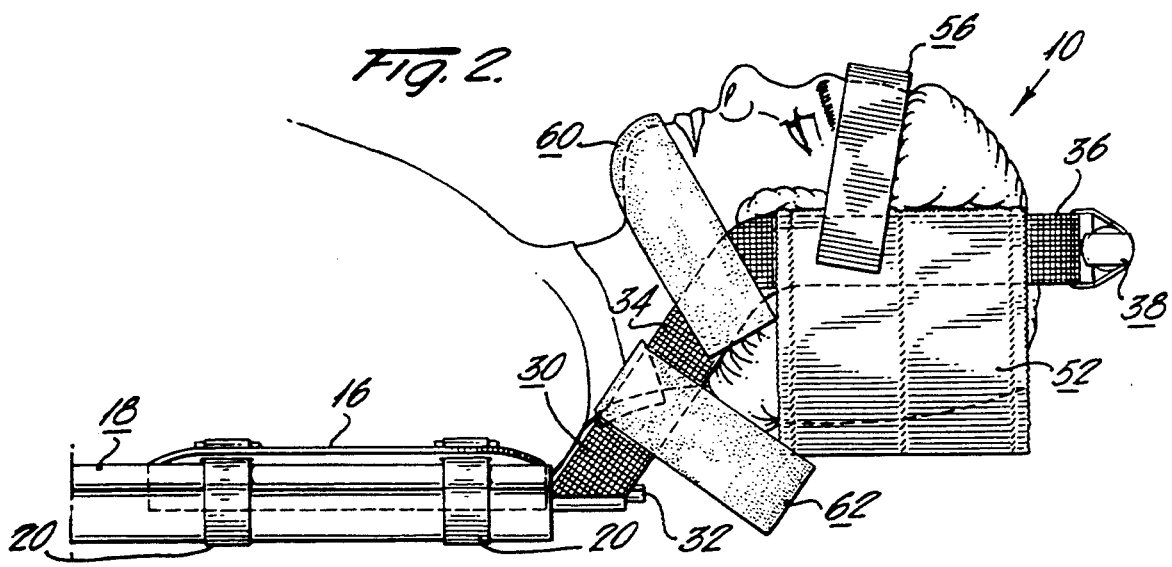

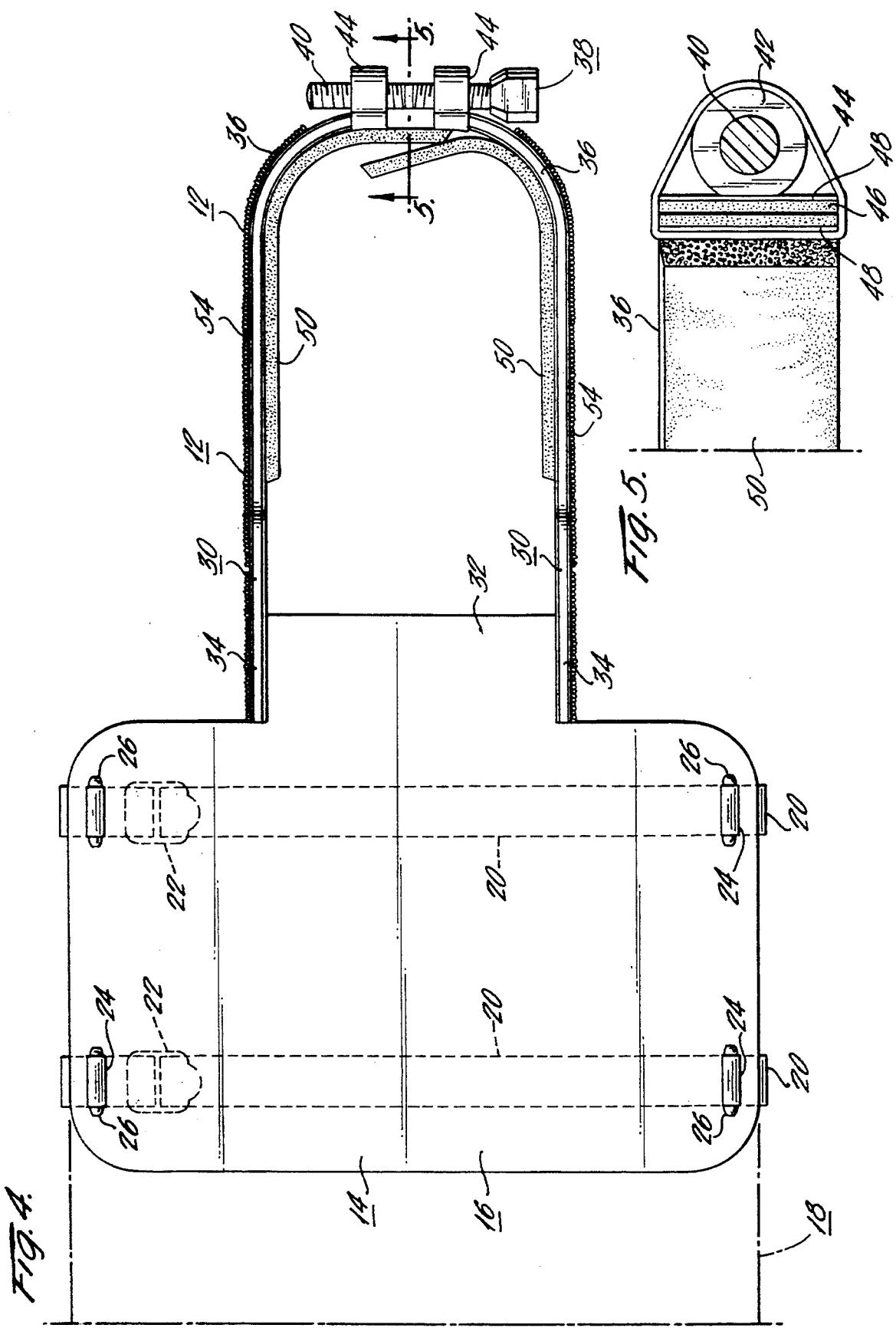

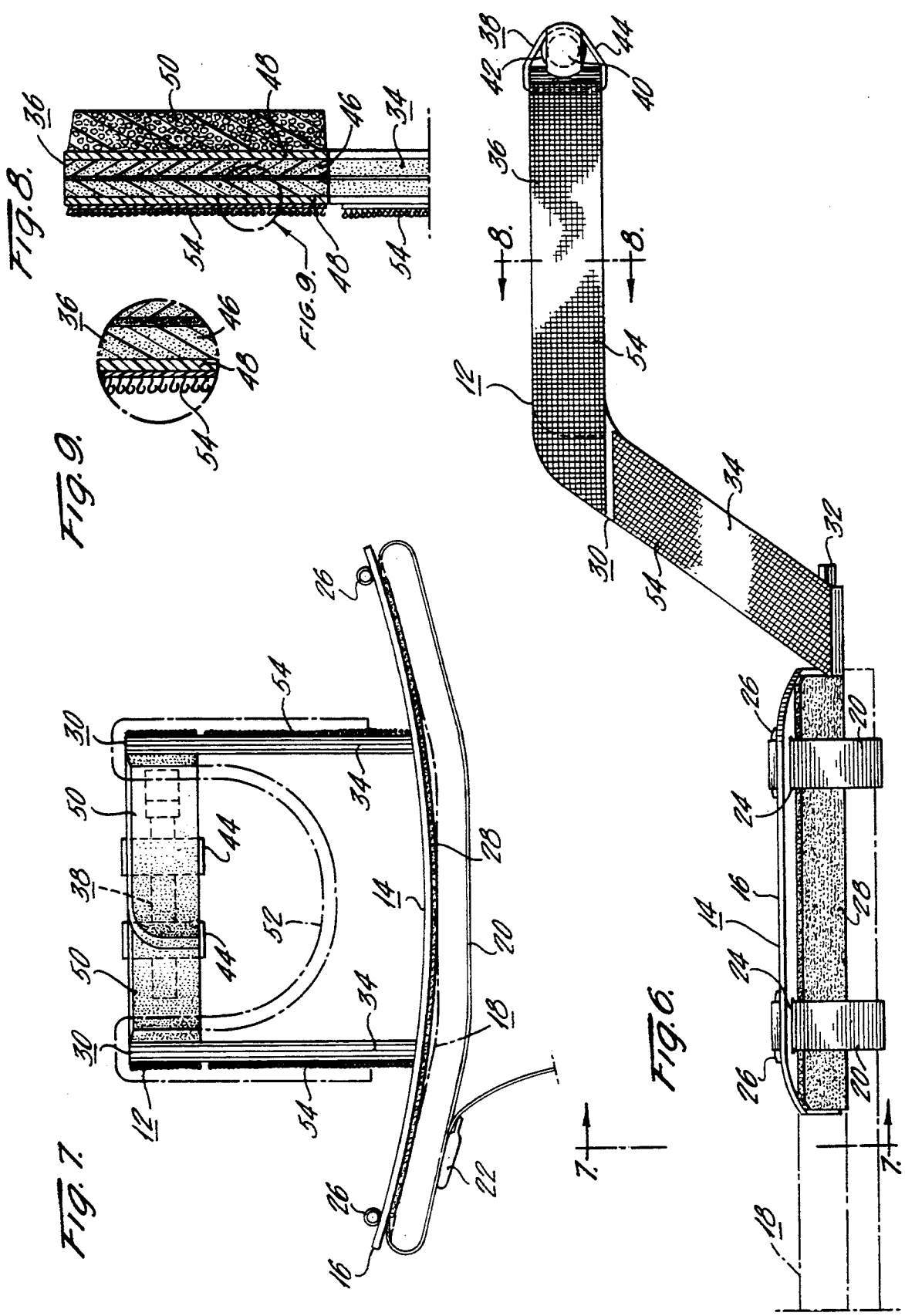

HEAD HOLDER FOR BRAIN TOMOGRAPHY

BACKGROUND OF THE INVENTION

During tomographic imaging of the brain, it is essential that the patient's head be held motionless in an optimal position throughout the procedure. Since an imaging session may require the head to be immobilized for an hour or more, the comfort of the patient is an important factor in achieving a successful examination.

Prior devices for supporting the head during tomographic imaging have typically comprised a trough or dish resting on or extending from a panel or tray on the examination table on which the patient is supported in a supine position. Because heads vary considerably in both size and shape, the trough or dish usually must be provided with a complement of foam pads, which are wedged under and around the head to achieve a head position which is optimal for the examination. The pads also serve to prevent head motion and provide some measure of comfort to the patient. The selection and placement of the pads by the technician can be a time consuming trial and error process which, while usually effective in obtaining the desired head position, is not always effective in immobilizing the head or providing comfortable support for the patient.

The principal shortcoming of previous devices is the reliance on padding for head positioning and restraint. Due to its resilient nature, the padding can allow some head displacement if the patient should twitch, especially if it is not packed tightly enough between the head and head support structure. Since any head movement can blur the image produced, repetition of the procedure may be necessary in some cases.

A further problem with the use of selective padding to position the head is the difficulty in determining whether the comfort level established initially for the patient will be adequate over the lengthy course of the examination. It may turn out, particularly for patients with spinal injuries, that what seemed comfortable at the beginning of the procedure becomes unbearably painful before its completion, necessitating the interruption of the procedure.

In addition to the described problems of inadequate restraint and patient comfort, prior head restraint devices are generally unsuitable for nuclear medicine imaging due to the interference by the head support structure with the imaging radiation. This can create shadows on the image which complicate the reading of the image and could even lead to a misinterpretation of the image.

It is furthermore highly desirable in nuclear medicine imaging, particularly with SPECT (single photon emission computed tomography), to have the camera as close to the patient's head as possible, and prior head support devices generally do not permit the close camera proximity desired.

SUMMARY OF THE INVENTION

The present invention comprises a panel adapted for attachment to the patient support surface of an imaging machine in a position underlying the shoulders of a patient. Extending from the head end of the panel is a head frame assembly comprising a pair of spaced, parallel, upstanding head frame elements which flank the neck of the patient and include substantially horizontal parallel portions which embrace the head of the patient. Adjustment means are provided connecting the free ends of the head frame elements which permits the selective adjustment of the horizontal spacing of the head frame elements to snugly grip the patient's head therebetween. The head frame assembly is of a non-metallic, imageable construction, formed preferably of a light-weight composite.

A flexible head sling extending between the head frame elements is adjustably attached to at least one head frame element. The head sling supports the weight of the patient's head and its adjustability permits the desired degree of head elevation. The sling conforms to the head contour, and is thus extremely comfortable, there being no pressure points as with conventional head supports. In the preferred embodiment, the sling is made of a looped fabric, and a strip of hooked fabric is attached to the outer face of each head frame element, thus providing the infinite adjustment capability characteristic of a hook and loop fastener.

To further insure the immobilization of the patient's head, a neck support strap may be provided extending between the head frame elements, the neck support strap also being adjustable such as by hook and loop attachment to facilitate the proper positioning of the strap. A chin restraining strap is provided which is adjustable in the same manner as the neck support strap. An adjustable forehead retraining strap is also provided, and its ends preferably include a strip of hooked fabric to cooperatively engage the looped head sling fabric which they overlie.

It is accordingly a first object of the present invention to provide a head support for brain tomography which will effectively immobilize the patient's head in the desired position for the duration of the procedure.

A further object of the invention is to provide a head support as described which may be quickly adjusted to provide the desired head position.

Another object of the invention is to provide a head support as described which gives the patient a high degree of comfort for any selected head position.

A still further object of the invention is to provide a head holder as described which will not interfere with the clarity of the imaging process.

Still another object of the invention is to provide a head holder as described which will permit the camera in nuclear medicine tomography to come extremely close to the patient's head, especially in the area of the brain stem.

Another object of the invention is to provide a head holder as described which will permit tomographic imaging of the neck area of the patient.

A further object of the invention is to provide a head holder as described which will accommodate a wide range of head sizes and shapes.

A further object of the invention is to provide a head holder as described which is of a simple, economically manufactured design, and which can be readily attached to and detached from the patient support table of tomographic equipment.

Additional objects and advantages of the invention will be more readily apparent from the following detailed description of a preferred embodiment of the invention.

BRIEF DESCRIPTION OF THE DRAWINGS

FIG. 1 is an isometric view of a head holder assembly in accordance with the present invention with the neck support strap, chin restraining strap, head sling and forehead restraining strap being shown in spaced relation to the head frame assembly;

FIG. 2 is a side elevational view showing the head holder assembly of FIG. 1 strapped to a table and a patient's head secured within the head frame assembly;

FIG. 3 is a greatly enlarged sectional view taken along line 3—3 of FIG. 1 showing details of the head supporting sling;

FIG. 4 is an enlarged plan view of the head holder frame assembly shown attached to a table (partly shown in broken lines);

FIG. 5 is an enlarged sectional view taken along line 5—5 of FIG. 4 showing details of the head frame element adjustment mechanism;

FIG. 6 is a side elevational view of the head holder frame assembly as shown in FIG. 4;

FIG. 7 is an end elevational view of the head holder taken along line 7—7 of FIG. 6 and additionally showing in broken lines the relaxed position of the head sling;

FIG. 8 is an enlarged sectional view taken along line 8—8 of FIG. 6 showing details of the head frame element construction; and FIG. 9 is a greatly enlarged sectional view of the circled area of FIG. 8 designated FIG. 9.

DETAILED DESCRIPTION OF PREFERRED EMBODIMENTS

Referring to the drawings and particularly FIGS. 1, 4, 6 and 7 thereof, a head support assembly generally designated 10 is illustrated which comprises a head frame assembly 12 extending from a frame support means 14. In the preferred embodiment, the frame support means comprises a mounting panel 16 curved to conform to the shape of a typical imaging machine patient support table 18 as shown in solid lines in FIG. 2 and in broken lines in FIGS. 4 and 6. A pair of straps 20 adjustable by means of buckles 22 extend beneath the panel 16 and permit its demountable attachment to the table 18, the belts passing underneath the table as shown in FIG. 7. The ends of the belts pass through slots 24 in the panel and are secured by means of pins 26 passing through loops sewn in the belt ends. A felt pad 28 on the bottom of the panel engages the table top, serving as a buffer between the two hard surfaces. The panel 16 is preferably made of a light weight fiber reinforced plastic material, such as a carbon fiber reinforced epoxy.

Although the frame support means 14 could comprise something other than the illustrated panel 16, for example the table itself, the panel arrangement is preferred since the present head support assembly can be quickly mounted on or dismounted from the table simply by tightening or loosening the straps 20, thus freeing the table for other uses.

The head frame assembly 12 comprises a pair of head frame elements 30 extending from a neck portion 32 of the panel 16 which, as shown in FIG. 2, underlies the neck of the patient. Each head frame element 30 includes an upstanding leg portion 34 attached at its lower end to the panel and a substantially horizontal head clamping portion 36 extending from the upper end of the leg portion. Although the leg portions 34 in the illustrated embodiment are angled upwardly and outwardly from the panel neck portion, in other embodiments having a more extended neck portion of the panel, the leg portions may extend more vertically since they will then clear the patient's shoulders. Also, the panel neck portion 32 may if desired be raised above the remainder of the panel and configured to conform to the shape of a human neck, in which case the leg portions 34 of the head frame elements 30 will be somewhat shorter and more nearly vertical.

The head clamping portions 36 of the head frame elements 30 extend in substantially parallel spaced relation, being sufficiently spaced to receive the head of the patient therebetween as shown in FIG. 2. The free ends of the head clamping portions 36 extend beyond the patient's head and preferably are curved inwardly toward each other to facilitate the attachment of adjustment means 38 for adjusting the spacing between the two head clamping portions 36. In the illustrated embodiment, the adjusting means 38 comprises an adjusting screw 40 which is threadedly engaged with round nuts 42 attached to the free ends of the head frame elements 30 by bands 44 as best seen in FIGS. 4 and 5. One half of the screw 40 is a right hand thread while the other half is a left hand thread so that turning of the screw in one direction will bring the head clamping portions 36 closer together while rotation in the other direction will move them farther apart.

The adjustment means 38 serves both to provide adjustment of the spacing of the head clamping portions as well as to structurally couple the ends of the head frame elements to provide rigidity to the head frame structure. The head frame elements are quite thin in lateral section but are preferably formed of a strong composite such as a structural foam 46 sandwiched between layers 48 of carbon fiber reinforced plastic as shown in the enlarged view of FIG. 8. Using such materials, the frame elements 30 can be on the order of 0.25 inches thick but still have sufficient rigidity so as not to deform or flex should the patient twitch. With such a construction, the head frame elements, which should ideally be positioned above the ears of the patients, do not extend laterally beyond the ears of the patient and thus permit a camera path very close to the patient's head. This is extremely important in SPECT imaging wherein the camera path actually follows the configuration of the patient's head to gain the best image resolution. The present head frame assembly minimizes the lateral protrusion of the head support and, being formed of an imageable material, is particularly well suited for nuclear medicine imaging techniques such as PET and SPECT. By selection of imageable materials for the adjustment means 38 as well as the frame elements 30, the frame assembly contains no metal structure which would cast shadows on the tomographic image. The screw 40 and nuts 42 are preferably made of a strong plastic material and the nuts 42 are connected to the frame element ends by bands 44 of a carbon fiber reinforced plastic such as an epoxy.

The thin composite construction described is utilized throughout the frame assembly and this allows continuous imaging beyond the head area, i.e. neck and upper spin, without image degradation.

The inner surfaces of the frame element head clamping portions 36 are lined with strips 50 of a relatively dense resilient foam to provide some cushioning between the head and the head frame elements. These strips are quite thin, on the order of 0.25 inches, so as to prevent patient movement and also to minimize the bulk, particularly the lateral protrusion, of the head frame.

The weight of the patient's head is supported by a head sling 52 which is adjustably supported between the head frame element head clamping portions 36. In the preferred embodiment, the sling 52 is adjustably attached to each head frame element by means of hook and loop fasteners, the sling comprising a looped fabric, and the outer surface of each head frame element 30 being covered by a strip 54 of hooked fabric adhesively secured thereto as illustrated in the greatly enlarged view of FIG. 9. The sling will conform to the shape of the patient's head, eliminating the possibility of hard spots that could become painful during a long procedure. By providing ample sling length, adjustment of the height of the head can be readily accomplished from either side of the head frame by simply lifting the overhanging sling end to disengage the sling loops from the frame hooks and then raising or lowering the head to the desired height, following which the sling end is simply pressed against the frame element to reengage the looped sling fabric with the frame element hooks. The technician can perform this adjustment with one hand, leaving the other hand free to support the patient's head.

To prevent upward head movement, a forehead restraining strap 56 is provided which extends across the patient's forehead and is secured to the head frame elements 30 by attachment to the head sling 52. The restraining strap 56 is made of hooked webbing and the head sling is looped on both sides as shown in the enlarged view of FIG. 3 to permit the strap 56 to be secured to it in any desired position. A resilient pad 58 of high density foam is provided centrally on the strap 56 for patient comfort.

A chin restraining strap 60 is also provided to supplement the forehead restraining strap 56 in preventing vertical head motion as well as pivotal head motion about a lateral axis. The strap 60 is preferably made of a foam material having a looped fabric surface and sold under the name Velafoam by Velcro, Inc. The strap 60 can be positioned as desired and attaches to the head frame element hooks in the same manner as the head sling.

A neck supporting strap 62 may be used if desired to tilt the head to the desired attitude or to provide additional comfort to the patient. The strap 62 is preferably made of the same material as the chin restraining strap and attaches to the head frame elements in the same manner.

For use of the present head holder, the panel is placed on the table of an imaging machine and the straps are tightened to secure it in place. The head frame adjusting screw is then turned to separate the head clamping portions 36 of the head frame elements 30 sufficiently to receive the head of the patient. With the patient lying in a supine position on the table with his shoulders on the panel, the patient's head is introduced into the head holder between the head frame elements 30. The head sling is adjusted to provide the optimal elevation and angle of the head for the particular imaging process involved, and the neck support strap added and adjusted if needed to supplement the head sling in providing the desired attitude of the head. The frame adjusting screw is then tightened to a firm but comfortable degree of tightness to clamp the head against lateral movement. The forehead restraining strap and the chin restraining straps are then applied to complete the immobilization of the patient's head.

The removal of the head from head support is quickly accomplished by removal of the chin and forehead restraining straps and the loosening of the adjusting screw to allow the head to be lifted from the head frame assembly.

Although hook and loop attachment is the preferred arrangement for adjustable connection of the head sling, neck supporting strap, and chin and forehead restraining straps, other arrangements might be used, such as straps and buckles. However, the simplicity and ease of use of the hook and loop system are important factors which favor its use.

The adjusting means for connecting the ends of the head frame elements 30 could optionally comprise a strap and buckle or possibly a hook and loop arrangement. However, as mentioned, it is important to provide structural rigidity to the assembly, and if such optional adjusting means were employed, some additional means would be necessary to join the frame element ends, such as a tubular member for receiving the ends. The use of a large screw with large nuts provides this needed rigidity and also provides a positive positioning of the frame element ends whether or not a head is positioned in the head holder assembly.

For nuclear medicine imaging, the preferred materials for the head frame as described are a low density foam, carbon fiber reinforced epoxy composite. This provides very high strength, light weight, permits a very thin wall structure and casts virtually no shadow on the image. Such a construction is also suitable for use with CT and X-ray imaging.

For MR imaging, the carbon fiber cannot be used because of its conductivity, but other reinforcing fibers such as Kevlar, S-2 fiberglass, or Spectra could be employed in its place.

Manifestly, changes in details of construction can be effected by those skilled in the art without departing from the invention.

What is claimed is:

1. A head support assembly for immobilizing the head of a patient during brain tomography comprising; a mounting panel adapted for demountable attachment to a patient support table, a head frame assembly extending from said mounting panel, said head frame assembly comprising a pair of upstanding head frame elements, each said head frame element being fixedly secured at a first end thereof to said mounting panel, said head frame elements each including a substantially horizontal head clamping portion extending in elevated relation to said mounting panel, said head clamping portions being disposed in spaced substantially parallel relation to receive the patient's head therebetween, adjustment means connecting the second ends of said head frame elements for adjusting the spacing of said head frame element head clamping portions, and an adjustable head support sling extending in a looped disposition between said spaced head clamping portions.

2. The invention as claimed in claim 1, wherein said head frame assembly including the head frame elements and the adjustment means are made of an non-metallic, imageable material.

3. The invention as claimed in claim 1, including at least one adjustable restraining strap attachable to said head frame elements for preventing vertical movement of the head.

4. The invention as claimed in claim 1, wherein said adjustment means comprises an adjustment screw.

5. A head support assembly for immobilizing the head of a patient during brain tomography and permitting the close proximity to the head of an orbiting tomographic camera comprising; a mounting panel adapted for demountable attachment to the patient support table of an imaging apparatus, a head frame assembly extending from said mounting panel, said head frame assembly comprising a pair of non-metallic imageable head frame elements, each said head frame element comprising an upstanding leg portion fixedly attached at its lower end to said mounting panel adjacent one edge thereof and a substantially horizontal head clamping portion extending from the upper end of said leg portion beyond said edge of said mounting panel, said head clamping portions being disposed in spaced substantially parallel relation to receive the patient's head therebetween, adjustment means connecting the free ends of said head frame elements for positively adjusting the spacing of said head frame element head clamping portions, a head sling for supporting the weight of the patient's head, said head sling extending in a looped disposition between said head clamping portions and being adjustably connected to at least one of said head clamping portions, and means extending between said head clamping portions for preventing the vertical movement of the patient's head.

6. The invention as claimed in claim 5, wherein said adjustment means comprises a screw extending between threaded elements on the ends of said head frame elements.

7. The invention as claimed in claim 5, wherein said head sling is adjustably attached to said head support elements by means of hook and loop fasteners.

8. The invention as claimed in claim 5, wherein said means for preventing vertical movement of the patient's head comprises at least one strap extending over the patient's head and being adjustably secured to at least one of said head frame elements.

9. A head support assembly for immobilizing the head of a patient during brain tomography and permitting the close proximity to the head of an orbiting tomographic camera comprising; a mounting panel adapted for demountable attachment to the patient support table of an imaging apparatus, a head frame assembly extending from said mounting panel, said head frame assembly comprising a pair of non-metallic imageable head frame elements, each said head frame element comprising an upstanding leg portion fixedly attached at its lower end to said mounting panel adjacent one edge thereof and a substantially horizontal head clamping portion extending from the upper end of said leg portion beyond said edge of said mounting panel, said head clamping portions being disposed in spaced substantially parallel relation to receive a patient's head therebetween, adjustment means connecting the free ends of said head frame elements for positively adjusting the spacing of said head frame element head clamping portions, a head sling for supporting the weight of the patient's head, said head sling extending in a looped disposition between said head clamping portions and being adjustably secured to at least one of said head clamping portions by means of hook and loop fasteners, and a head restraining strap adapted to pass over the head of the patient to prevent vertical movement thereof, said head restraining strap overlying said head clamping portions and said head sling and being adjustable with respect thereto by means of hook and loop fasteners.

10. The invention as claimed in claim 9, including a neck support strap adjustably extending between said head frame element leg portions.

11. The invention as claimed in claim 9, including a chin restraining strap adjustably attached to said head frame element leg portions by hook and loop fasteners.

12. The invention as claimed in claim 9, wherein said head frame element head clamping portions have a hooked fastener material on the outer face thereof, said head sling comprises a looped fabric on both sides thereof, and wherein said head restraining strap comprises hooked fasteners on one side thereof.

13. The invention as claimed in claim 9, wherein said adjustment means comprises a screw.

14. The invention as claimed in claim 9, wherein said head frame elements are formed of a thin walled composite material.

* * * * *